United States Patent [19]

Resemann et al.

[11] Patent Number: 4,581,177

[45] Date of Patent: Apr. 8, 1986

[54] PROCESS FOR THE PREPARATION OF 3-CYANO-4-AMINOACETOPHENONES

[75] Inventors: Wolfgang Resemann; Ferdinand Fraunberger, both of Biberach, Fed. Rep. of Germany

[73] Assignee: Dr. Karl Thomae GmbH, Biberach an der Riss, Fed. Rep. of Germany

[21] Appl. No.: 723,999

[22] Filed: Apr. 17, 1985

[51] Int. Cl.[4] .............................................. C07C 121/78
[52] U.S. Cl. ...................................... 558/415; 558/422
[58] Field of Search ..................................... 260/465 E

[56] References Cited
U.S. PATENT DOCUMENTS
4,404,222  9/1983  Baker et al. ........................ 424/304

OTHER PUBLICATIONS

A. Graham, Synthetic Communications 10(3)241–24 (1980).

Primary Examiner—Dolph H. Torrence
Attorney, Agent, or Firm—David E. Frankhouser; Alan R. Stempel; Charles J. Herron

[57]  ABSTRACT

A new process is disclosed for preparing 3-cyano-4-aminoacetophenone which, starting from 3-cyano-4-acetamidoacetophenone, enables this compound to be produced on an industrial scale in high yields.

3-Cyano-4-aminoacetophenone is an intermediate product for the preparation of 2-amino-5-[1-hydroxy-2-(alkyl- or dialkyl-amino)ethyl]benzonitriles which show $\beta_2$-mimetic activities and may be used as feed additives.

3 Claims, No Drawings

PROCESS FOR THE PREPARATION OF 3-CYANO-4-AMINOACETOPHENONES

The invention relates to a new process for the preparation of certain 3-cyano-4-aminoacetophenones.

The 3-Cyano-4-aminoacetophenones of interest herein have the formula

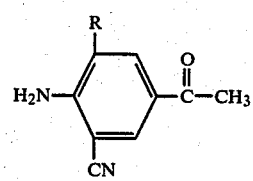

(I)

wherein R is a hydrogen or fluorine atom.

These compounds are important intermediate products in the preparation of valuable pharmaceutical compositions and feed activities. As feed additives, the compounds of formula V described hereinafter bring about more intensive use of food when used for fattening, lead to more rapid growth in animal husbandry and an increase in the ratio of lean meat to fat in the utilisation of animals.

In view of the worldwide shortage of high-grade protein there is considerable interest in such active substances. In order to provide sufficient quantities of these active substances the discovery of a simple method of production which is environmentally favorable is urgently needed.

The 3-cyano-4-aminoacetophenones of formula I play an important role in the production of the active substances. It was therefore important to find a simple method of preparing them which ensures not only a high yield but also a high quality product.

The present invention embraces a method for preparing a compound of the above formula I which comprises treating a 3-cyano-4-acetamidoacetophenone of the formula

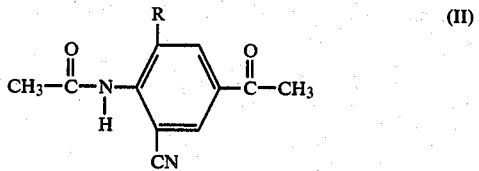

(II)

wherein R is as hereinbefore defined, with an alkali metal hydroxide or an alkali metal methoxide in methanol as solvent.

Suitable alkali metal hydroxides or methoxides are potassium hydroxide, sodium hydroxide, potassium methoxide and sodium methoxide. The use of potassium hydroxide is preferred.

The process provided by the present invention can conveniently be carried out by adding the 3-cyano-4-acetamidoacetophenone of formula II to a solution comprising the base and methanol. The solution is preferably heated to between about 30° to 50° C. prior to addition of the compound of formula II. The saponification of the compound of formula II can be accomplished at temperatures between about 40° C. and the boiling point of the reaction mixture. It is preferred, however, to bring the reaction mixture to reflux. The resulting compound of formula I can then be isolated by a conventional purification technique. In particular, if the reaction mixture is evaporated to dryness, the residue can be taken up in water and the solution mixed with an inorganic acid, preferably hydrochloric acid, whereupon the 3-cyano-4-aminoacetophenone of formula I will be obtained as a crystalline precipitate. The precipitate can then be washed and dried in order to yield the compound of formula I in substantially pure form. Generally, yields of between 80° and 90° C. of theory are achieved, depending upon the compound of formula II used. If R is a fluorine atom, yields are somewhat lower.

The deacylation of compounds of formula II cannot be carried out in either acidic or alkaline aqueous systems to give the desired result when using the conventional methods of saponification. The literature indicates [cf. A. Graham, Synthetic Communications 10(3)241–243 (1980)] that strong acids cannot be used because the presence of the reactive cyano groups adjacent to the acylamino group in the compound of formula II will cause cyclization to given an undesired product of the formula

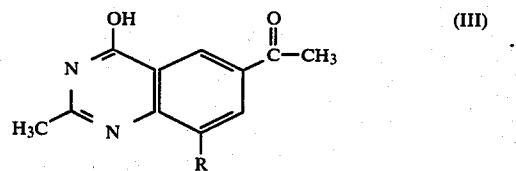

(III)

With dilute acids, there is formed the corresponding 2-acyl-aminobenzamide. Alkaline aqueous systems also cannot be used because the cyano group will be hydrolyzed to form an amide group.

When deacylation is performed using the method according to the present invention, it has unexpectedly been found that the acetyl group can be cleaved from the acylamino group without altering the cyano group. This result is possible only if an alkali metal hydroxide in methanol or an alkali metal methoxide in methanol are used to perform the saponification.

The starting compounds of formula II may be obtained, for example, by reacting a 3-bromo-4-acetamidoacetophenone of formula

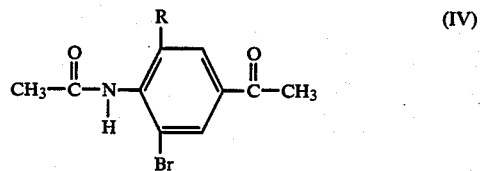

(IV)

wherein R is as hereinbefore defined, with copper (I) cyanide. To do this, the 3-bromo-4-acetamidoacetophenone of formula IV is reacted with copper (I) cyanide in a solvent such as pyridine or dimethylformamide at temperatures of between 100° and 150° C. and the product is purified, e.g. with ethyl acetate (cf. also Houben-Weyl Volume 8, Oxygen Compounds III, page 303).

The starting compounds of formula IV may be obtained, for example, from 4-acetamidoacetophenone (for the preparation see Beilstein E II, 14, 33) by bromination using bromine in the presence of glacial acetic acid/water [cf. L. C. Raiford, H. L. Davis, J. Am. Chem. Soc. 50, 158 (1928) and Beilstein E II, 14, 33].

The compounds of formula I are important intermediate products for the preparation of compounds of formula

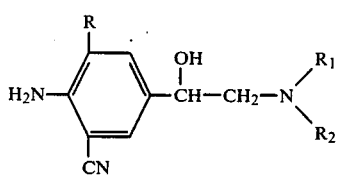

(V)

wherein R is as hereinbefore defined, $R_1$ is hydrogen or lower alkyl and $R_2$ is lower alkyl. The compounds of formula V may be used, for example, as feed additives and to bring about greater growth in carcass animals and poultry and also lead to increased utilisation of the feed. They also increase the ratio of lean meat to fat (cf. U.S. Pat. No. 4,407,819). Moreover, these compounds also have therapeutically useful properties, for example an effect on the $\beta$-receptors, particularly a $\beta_2$-mimetic activity. In a particularly valuable compound of general formula V R and $R_1$ are hydrogen atoms and $R_2$ is an isopropyl group (melting point 165°–167° C.).

The compounds of formula V may easily be prepared from 3-cyano-4-aminoacetophenones by the following steps:

(a) Bromination in the conventional solvents, such as glacial acetic acid, tetrahydrofuran, with elemental bromine or copper(II)bromide, (b) reaction of the resulting ω-bromo-3-cyano-4-aminoacetophenone with amines of formula $HNR_1R_2$ wherein $R_1$ and $R_2$ are as hereinbefore defined, to form the corresponding aminoketones at temperatures of up to 20° C., and (c) reduction of the aminoketone to form the aminoalcohol of formula V with the aid of sodium boronate in water.

The following Examples are intended to further illustrate the invention:

A. Examples of the preparation of the end products.

EXAMPLE 1

3-Cyano-4-aminoacetophenone 25.2 g (0.45 mol) of potassium hydroxide and 300 ml of methanol are placed in a reaction vessel and the contents of the vessel are heated to 40° C. Within 2 to 4 minutes 30 g (0.15 mol) of 3-cyano-4-acetamidoacetophenone is added and the reaction mixture is refluxed for 20 minutes. It is then concentrated by evaporation to dryness and the residue is mixed with 300 ml of water. Next 40 ml of concentrated hydrochloric acid is added and the 3-cyano-4-aminoacetophenone formed is precipitated in the form of crystals. The mixture is cooled to 10° C. and stirred for a further hour. After suction filtering and washing of the filter residue with water and drying this residue at 60° C., 21 g of beige 3-cyano-4-aminoacetophenone is obtained, corresponding to a yield of 87.5% of theory. Melting point: 161.5° C.

If sodium hydroxide and methanol are used in the same molar ratios and under the same reaction conditions, 3-cyano-4-aminoacetophenone is obtained in a yield of 80% of theory.

EXAMPLE 2

3-Cyano-4-aminoacetophenone 3.8 kg (59.6 mol) of potassium hydroxide and 45.6 liters of methanol are placed in a reaction vessel and the contents of the vessel are heated to 40° C. Within 5 to 10 minutes 4.58 kg (22.6 mol) of 3-cyano-4-acetamidoacetophenone is added. The mixture is refluxed for 25 minutes, the solvent is eliminated and 60 liters of water followed by 6 liters of concentrated hydrochloric acid are added to the dry residue. The workup is continued as described in Example 1.

Yield: 3.0 kg of 3-cyano-4-aminoacetophenone corresponding to 82.8% of theory.

Melting point: 161.5° C.

By using potassium methoxide instead of potassium hydroxide, a yield of 76% of theory was obtained.

EXAMPLE 3

3-Cyano-4-amino-5-fluoroacetophenone

Using the same method as in Example 1, 3-cyano-4-acetamido-5-fluoroacetophenone is saponified with potassium hydroxide at 45 to 50° C. with a reaction time of 24 hours to form 3-cyano-4-amino-5-fluoroacetophenone.

Yield: 55% of theory. With sodium hydroxide a yield of 48% of theory was obtained.

B. Example of the preparation of the starting compound 3-cyano-4-acetamidoacetophenone.

EXAMPLE 4

In accordance with Rosenmund-V. Braun's reaction described in Houben-Weyl, Volume 8, Oxygen Compounds III, page 303, 70 g (0.273 mol) of 3-bromo-4-acetamido-acetophenone (prepared using the method of L. C. Raiford, H. L. Davis, J.Am.Chem.Soc. 50, 158 (1928)) and 24,5 g (0,273 mol) of copper (I) cyanide are heated in 150 ml of dimethylformamide in an oil bath to 130° C. for 2.5 hours. Copper(I) bromide is precipitated, which is suction filtered at the end of the reaction, using a suction filter at 95° C., and washed with 20 ml of dimethylformamide. The warm filtrate is poured into 300 ml of water, whereupon the 3-cyano-4-acetamidoacetophenone and the remaining copper(I) bromide are precipitated. The suspension is stirred for a further 2 hours and suction filtered and the filter residue is washed with water. The crude product, dried at 60° C. is decocted first with 700 ml of ethyl acetate and again with 300 ml of ethyl acetate in order to eliminate the copper salt. The combined extracts are evaporated down to a total volume of 200 ml. In order to complete the precipitation, a further 200 ml of petroleum ether (60°/70° C.) are added to the warm ethyl acetate suspension. After cooling and suction filtering, the filter residue is dried at 60° C. until a constant weight is obtained.

Yield: 36 g of 3-cyano-4-acetamidoacetophenone corresponding to 62.5% of theory, based on the 3-bromo-4-acetamidoacetophenone used.

Melting point: 170° C.

What is claimed is:

1. A method for preparing 3-cyano-4-aminoacetophenones of the formula wherein R is a hydrogen or fluorine atom, which method comprises treating a 3-cyano-4-acetamidoacetophenone of the formula

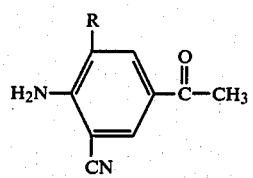
(I)

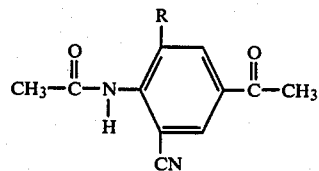
(II)

wherein R is as hereinbefore defined, with a base selected from the group consisting of potassium hydroxide, sodium hydroxide, potassium methoxide and sodium methoxide, in the presence of methanol as solvent.

2. The method of claim 1 wherein potassium hydroxide in methanol is used.

3. The method of claim 2 further wherein the compound of formula II is added to a potassium hydroxide-methanol solution which is at a temperature between 30° to 50° C., the resulting reaction mixture is subsequently heated to between about 40° C. and the reflux temperature of said mixture, the solvent methanol is eliminated by evaporation, the residue is dissolved in water, and the end product is precipitated by acidification.

* * * * *